US012629346B2

(12) United States Patent
Nagaike et al.

(10) Patent No.: US 12,629,346 B2
(45) Date of Patent: May 19, 2026

(54) PATCH

(71) Applicant: Kobayashi Pharmaceutical Co., Ltd., Osaka (JP)

(72) Inventors: Daisaku Nagaike, Dalton, GA (US); Tsuyoshi Igaue, Dalton, GA (US)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 1234 days.

(21) Appl. No.: 17/418,415

(22) PCT Filed: Dec. 26, 2019

(86) PCT No.: PCT/IB2019/061379
§ 371 (c)(1),
(2) Date: Jun. 25, 2021

(87) PCT Pub. No.: WO2020/136605
PCT Pub. Date: Jul. 2, 2020

(65) Prior Publication Data
US 2022/0142951 A1 May 12, 2022

Related U.S. Application Data

(60) Provisional application No. 62/785,348, filed on Dec. 27, 2018.

(51) Int. Cl.
*A61K 31/167* (2006.01)
*A61K 9/70* (2006.01)
(Continued)

(52) U.S. Cl.
CPC .......... *A61K 31/167* (2013.01); *A61K 9/7061* (2013.01); *A61K 31/045* (2013.01); *A61P 23/02* (2018.01)

(58) Field of Classification Search
None
See application file for complete search history.

(56) References Cited

U.S. PATENT DOCUMENTS 5,741,510 A * 4/1998 Rolf ..................... A61K 9/7023
424/448
6,469,227 B1 * 10/2002 Cooke ...................... A61K 9/70
424/443
(Continued)

FOREIGN PATENT DOCUMENTS

JP      2000-185069 A      7/2000
JP      2001-104359 A      4/2001
(Continued)

OTHER PUBLICATIONS

International Search Report issued in corresponding International Patent Application No. PCT/IB2019/061379 dated Mar. 10, 2020.
(Continued)

*Primary Examiner* — Isis A Ghali
(74) *Attorney, Agent, or Firm* — Morgan, Lewis & Bockius LLP

(57) ABSTRACT

A patch (10) comprising: a nonwoven fabric (1); and an adhesive layer (2) on the nonwoven fabric (1), wherein the adhesive layer (2) comprises a cool feeling agent, a local anesthetic and/or an anti-inflammatory analgesic, and water, and the adhesive layer (2) has a maximum thickness of 0.50 mm or more.

19 Claims, 1 Drawing Sheet

(51) Int. Cl.
    *A61K 31/045*     (2006.01)
    *A61P 23/02*     (2006.01)

(56)             References Cited

U.S. PATENT DOCUMENTS

| | | | |
|---|---|---|---|
| 7,018,647 B1 * | 3/2006 | Yamasaki | A61P 29/00 |
| | | | 424/443 |
| 2006/0198802 A1 | 9/2006 | Ito et al. | |
| 2007/0292491 A1 * | 12/2007 | Hansen | A61K 8/0241 |
| | | | 424/443 |
| 2011/0184066 A1 | 7/2011 | Nazuki | |
| 2020/0009075 A1 | 1/2020 | Tsurushima et al. | |

FOREIGN PATENT DOCUMENTS

| | | | |
|---|---|---|---|
| JP | 2002-241747 A | | 8/2002 |
| JP | 2005-111159 A | | 4/2005 |
| JP | 2006-087656 A | | 4/2006 |
| JP | 2007-119552 A | | 5/2007 |
| JP | 2014152172 A | * | 8/2015 |
| JP | 2018-083069 A | | 5/2018 |
| TW | 200510005 A | | 3/2005 |
| TW | 200942275 A1 | | 10/2009 |
| TW | 201841657 A | | 12/2018 |
| WO | 2006/112533 A1 | | 10/2006 |

OTHER PUBLICATIONS

Written Opinion issued in corresponding International Patent Application No. PCT/IB2019/061379 dated Mar. 10, 2020.

* cited by examiner

PATCH

TECHNICAL FIELD

The present disclosure relates to a patch.

BACKGROUND ART

Conventionally, patch-type coolants have been used for cooling the body after exercise, preventing or improving heat disorders such as heat illness, preventing or improving inflammation of the skin, preventing or alleviating swelling, and promoting blood circulation and the like. Examples of such patch-type coolants include those with an adhesive layer supported on a support such as non-woven fabric, which cools the portion where the patch is attached by the heat of vaporization of water.

For example, Patent Literature 1 discloses a sheet-shaped coolant having an adhesive layer with a pre-determined composition from the view point of durability of a cooling effect. Furthermore, Patent Literature 2 discloses a patch for cooling the body, which has an adhesive layer that resists freezing even when stored in a freezer, for the purpose of giving an increased coolness.

CITATION LIST

Patent Literature

[Patent Literature 1] Japanese Patent Laid-Open No. 2002-241747
[Patent Literature 2] Japanese Patent Laid-Open No. 2018-83069

SUMMARY OF INVENTION

Technical Problem

Recent patch-type coolants have been used for a wide range of applications and now are required to have additional effects such as an anti-inflammatory effect and an analgesic effect as well as a cool feeling effect. Thus, a patch with a structure that can maintain both a cool feeling effect and additional effects such as an anti-inflammatory effect and an analgesic effect for a long time has been required.

The present disclosure provides a patch that has been made in view of such problems, and one object of the patch described herein is to maintain a cool feeling effect and an analgesic effect for a longer time.

Solution to Problem

The present inventors have conducted intensive studies to solve the above problem. As a result, the present inventors have found that the above problem can be solved by using an adhesive layer with a pre-determined structure, and have completed the present invention.

In one aspect, the present disclosure provides the following patch.

[1] A patch comprising:
a nonwoven fabric; and
an adhesive layer on the nonwoven fabric,
wherein the adhesive layer comprises (i) a cool feeling agent, (ii) a local anesthetic and/or an anti-inflammatory analgesic and (iii) water, and
the adhesive layer has a maximum thickness of 0.50 mm or more.

[2] The patch according to [1], wherein the local anesthetic comprises lidocaine.
[3] The patch according to [1] or [2], wherein the cool feeling agent comprises menthol.
[4] The patch according to any one of [1] to [3], wherein an area to which the adhesive layer is applied is smaller than an area of the nonwoven fabric, the adhesive layer has an outer edge portion whose thickness is gradually reduced toward an edge, and an angle formed by a side surface of gel and the nonwoven fabric in the outer edge portion is 5° or more and less than 90°.
[5] The patch according to any one of [1] to [4], wherein the adhesive layer has an adhesive force of 10 to 100 gf/cm$^2$.
[6] The patch according to any one of [1] to [5], wherein the adhesive layer has a maximum thickness of 1.00 mm or more.
[7] The patch according to any one of [1] to [6], further comprising an infiltration layer in which part of the adhesive layer infiltrates into the nonwoven fabric, wherein the infiltration layer has a maximum thickness of 0.001 to 0.500 mm.
[8] The patch according to any one of [1] to [7], wherein a content of the cool feeling agent is 0.01 to 10% by weight based on a total amount of the adhesive layer.
[9] The patch according to any one of [1] to [8], wherein a total content of the local anesthetic and the anti-inflammatory analgesic is 1 to 7.5% by weight based on a total amount of the adhesive layer.
[10] The patch according to any one of [1] to [9], wherein a content of the cool feeling agent is 6.25 to 500 parts by weight based on a total of 100 parts by weight of the local anesthetic and the anti-inflammatory analgesic.
[11] The patch according to any one of [1] to [10], wherein a content of the water is 50 to 90% by weight based on a total amount of the adhesive layer.
[12] The patch according to any one of [1] to [11], wherein the adhesive layer comprises at least one member selected from the group consisting of aluminum hydroxide, sodium polyacrylate, polyacrylic acid and polyvinyl alcohol.

Advantageous Effect of Invention

In one aspect, the present disclosure provides a patch which can maintain a cool feeling effect and an analgesic effect for a longer time.

DESCRIPTION OF EMBODIMENTS

Figure 1:
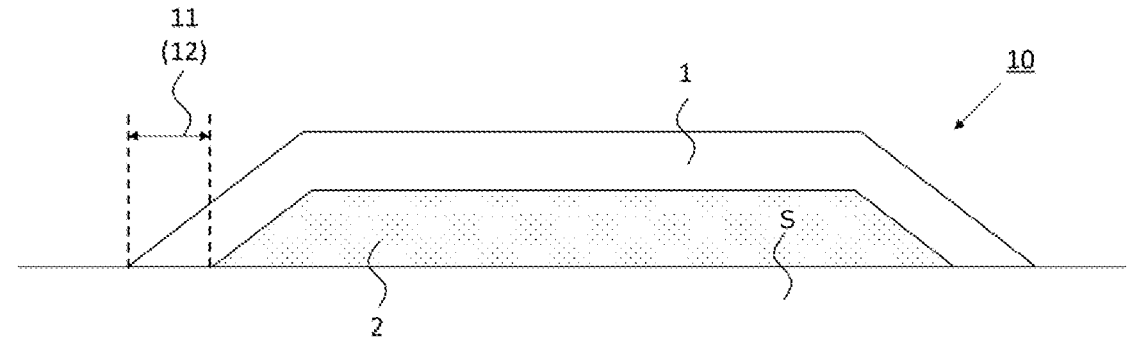
FIG. 1 shows a schematic view of a cross-section of a patch according to an embodiment of the present invention when the patch is attached to a target part.

Hereinafter, embodiments of the present disclosure (referred to as "the present embodiment" below) will be described in detail, but the present disclosure is not limited thereto. Various modifications may be made without departing from the gist of the embodiments of the present disclosure. In the figures, identical elements are marked by an identical symbol, and overlapping descriptions are omitted. Positional relations including vertical or horizontal relations are as described in the figures unless otherwise specified.

Furthermore, the dimensional ratio of the figures is not limited to the ratio illustrated in the figures.

Patch

The patch according to some embodiments includes a nonwoven fabric and an adhesive layer on the nonwoven fabric, and the adhesive layer includes a cool feeling agent, a local anesthetic and/or an anti-inflammatory analgesic and water, and the adhesive layer has a maximum thickness of 0.50 mm or more.

Nonwoven Fabric

The nonwoven fabric in the present embodiment is not particularly limited, and various known materials may be used. The fiber constituting the nonwoven fabric may be roughly classified into synthetic fibers and natural fibers. Non-limiting examples of the synthetic fibers include polyamide fibers; polyacrylic fibers; nylon fibers; polyolefin fibers such as polypropylene and polyethylene; polyester fibers such as polyethylene terephthalate and polybutylene terephthalate; rayon (regenerated fiber); vinylon; and aramid fibers.

Furthermore, non-limiting examples of the natural fibers include cotton, hemp, silk, wool, kenaf, bananas, bamboo, pulp and mineral fibers.

Examples thereof also include a mixed fiber thereof. Of them, polyester fibers are preferred from the viewpoint of improvement and durability of a cool feeling effect.

In one aspect, the nonwoven fabric has a thickness T of 0.50, 0.60, 0.70, 0.80, 0.90, 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.10, 3.20, 3.30, 3.40, 3.50, 3.60, 3.70, 3.80, 3.90, 4.00, 4.10, 4.20, 4.30, 4.40, 4.50, 4.60, 4.70, 4.80, 4.90 mm or more. In another aspect, the nonwoven fabric has a thickness T of 0.60, 0.70, 0.80, 0.90, 1.00, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.10, 3.20, 3.30, 3.40, 3.50, 3.60, 3.70, 3.80, 3.90, 4.00, 4.10, 4.20, 4.30, 4.40, 4.50, 4.60, 4.70, 4.80, 4.90, 5.00 mm or less. In some embodiments, the nonwoven fabric has a thickness T of preferably 0.50 to 5.00 mm, preferably 1.00 to 4.00 mm, and preferably 1.00 to 3.00 mm. When the thickness T of the nonwoven fabric is in the above range, a cool feeling effect due to vaporization of water and a heat dissipation effect by heat exchange with the atmosphere may be improved. Thus, a cool feeling effect is likely to be improved and maintained. For the thickness of the nonwoven fabric, for example, a patch is cut in the direction perpendicular to the surface direction, and the thickness of the nonwoven fabric in the resulting cross-section may be measured with a caliper. Alternatively, the thickness of the nonwoven fabric in a cross-section may be measured in an image of the cross-section photographed by, for example, a microscope.

A basis weight is measured as a weight of the fabric sheet cut to a basic size, for example, weight gram per m² of the fabric sheet. In one aspect, the basis weight of the nonwoven fabric is 10, 20, 30, 40, 50, 60, 70, 80, 90, 100, 110, 120, 130, 140, 10, 160, 170, 180, 190, 200, 210, 220, 230, 240, 250 g/m² or more. In another aspect, the basis weight of the nonwoven fabric is 500, 490, 480, 470, 460, 450, 440, 430, 420, 410, 400, 390, 380, 370, 360, 350, 340, 330, 320, 310, 300, 290, 280, 270, 260, 250 g/m² or less. In some embodiments, the basis weight of the nonwoven fabric is preferably 10 to 500 g/m², preferably 20 to 400 g/m², and preferably 50 to 250 g/m². When the basis weight of the nonwoven fabric is in the above range, a cool feeling effect due to vaporization of water and a heat dissipation effect by heat exchange with the atmosphere may be improved. Thus, a cool feeling effect is likely to be improved and maintained.

The support may have a monolayer structure of a single material, or may have a multiple layer structure in which two or more of the same or different materials are stacked. The shape of the support is not particularly limited, and may be suitably determined based on the shape of the part of the body to which the patch is attached.

Adhesive Layer

The adhesive layer includes (i) a cool feeling agent, (ii) a local anesthetic and/or an anti-inflammatory analgesic and (iii) water, and if necessary, a gel substrate for forming a water-containing gel, and other components. The respective components will be described in detail below.

Cool Feeling Agent

In some embodiments, a cool feeling agent may be an agent having a boiling temperature of 35° C. or less, or evoking cold sensation via cold receptors on the skin, including transient receptor potential melastatin 8 (TRPM8). In some embodiments, cool feeling agents are not particularly limited, and examples thereof include menthol, N-ethyl-p-menthane-3-carboxamide, N-(ethoxycarbonylmethyl)-3-p-menthane carboxamide, N,2,3-trimethyl-2-isopropyl butaneamide, 3-(L-methoxy)propane-1,2-diol, menthyl lactate, monomenthyl succinate, menthone glycerin acetal, 3-1-menthoxypropane-1,2-diol, menthone glycerin ether, spilanthol, monomenthyl succinate, oxalic acid menthyl ethyl amide, menthyl pyrrolidone carboxylate, and menthane carboxamide ethylpyridine. In some embodiments, the cool feeling agent may comprise menthol to improve a cooling effect and durability of a cool feeling effect and durability of an analgesic effect. One of these cool feeling agents may be used alone, or two or more of them may be used in combination.

The cool feeling agent may be used in the form of a mixture. For example, menthol may be used in the form of an essential oil such as mint oil, peppermint oil and spearmint oil. The cool feeling agent also includes a pharmaceutically acceptable salt.

The content of the cool feeling agent may be determined by those skilled in the art depending on the desired level of the cool feeling effect. The content of the cool feeling agent is, for example, 0.01 to 10% by weight, preferably 0.1 to 7.5% by weight, more preferably 0.5 to 5% by weight, and further preferably 0.75 to 5% by weight based on the total amount of the adhesive layer. When the content of the cool feeling agent is 0.01% by weight or more, a cool feeling effect tends to be improved, and not only durability of a cool feeling effect but also durability of an analgesic effect tend to be improved. When the content of the cool feeling agent is 10% by weight or less, irritation due to an excessive cool feeling effect tends to be suppressed.

Local Anesthetic and Anti-Inflammatory Analgesic

The local anesthetic in the present embodiment is not particularly limited, and examples thereof include lidocaine, procaine, tetracaine, dibucaine, mepivacaine, prilocaine and bupivacaine. Of them, lidocaine is preferred from the viewpoint of durability of an analgesic effect. The local anesthetic also includes a pharmaceutically acceptable salt.

The anti-inflammatory analgesic in the present embodiment is not particularly limited, and examples thereof include ibuprofen, diclofenac, methyl salicylate, glycol salicylate, indomethacin, felbinac, piroxicam and flurbiprofen. Of them, ibuprofen and diclofenac are preferred because they provide excellent durability of a cool feeling effect and excellent durability of an analgesic effect. The anti-inflammatory analgesic also includes a pharmaceutically acceptable salt.

The pharmaceutically acceptable salt may be an inorganic salt or an organic salt. The salt is not particularly limited, and examples thereof include monobasic acid salts such as hydrochloride, hydrobromide and methanesulfonate; and polybasic acid salts such as fumarate, maleate, citrate and tartrate. One of these local anesthetics and anti-inflammatory analgesics may be used alone, or two or more of them may be used in combination.

The total content of the local anesthetic and the anti-inflammatory analgesic may be determined by those skilled in the art in consideration of, for example, efficacy and skin penetration. The total content of the local anesthetic and the anti-inflammatory analgesic is, for example, preferably 1 to 7.5% by weight, more preferably 1.5 to 6% by weight, and further preferably 2 to 5% by weight based on the total amount of the adhesive layer. When the total content of the local anesthetic and the anti-inflammatory analgesic is 1% by weight or more, the analgesic effect tends to be improved and durability of the analgesic effect tends to be improved.

In one aspect, the content of the cool feeling agent is 6, 7, 8, 9, 10, 11, 12, 13, 14, 15, 16, 17, 18, 19, 20 or more parts by weight based on a total of 100 parts by weight of the local anesthetic and the anti-inflammatory analgesic. In another aspect, the content of the cool feeling agent is 7, 8, 9, 10, 11, 12, 13, 14, 15, 16, 17, 18, 19, 20, 30, 40, 50, 60, 70, 80, 90, 100, 150, 200, 250, 300, 350, 400, 450, 500 or more parts by weight based on a total of 100 parts by weight of the local anesthetic and the anti-inflammatory analgesic. The content of the cool feeling agent is preferably 6.25 to 500 parts by weight, preferably 10 to 150 parts by weight, preferably 20 to 125 parts by weight, and preferably 20 to 100 parts by weight based on a total of 100 parts by weight of the local anesthetic and the anti-inflammatory analgesic. When the ratio of the content of the cool feeling agent to the content of the local anesthetic and the anti-inflammatory analgesic is within the above range, the local anesthetic and/or the anti-inflammatory analgesic are unlikely to inhibit the cool feeling action of the cool feeling agent.

Water

In one aspect, the content of water is 50, 51, 52, 53, 54, 55, 56, 57, 58, 59, 60% by weight or more based on the total amount of the adhesive layer. In another aspect, the content of water is 90, 80, 70, 60% by weight or less based on the total amount of the adhesive layer. In some embodiments, the content of water is preferably 50 to 90% by weight, preferably 50 to 80% by weight, and preferably 55 to 70% by weight based on the total amount of the adhesive layer. When the content of water is within the above range, a cool feeling effect due to heat of vaporization tends to be improved, and durability of the cool feeling effect and durability of the analgesic effect tend to be improved.

Gel Substrate

The gel substrate is not particularly limited, and for example, those which make the adhesive layer water-retainable and control flowability of the adhesive layer to maintain a predetermined shape are preferred. Using a gel substrate makes the adhesive layer being in the form of a water-containing gel which is adhesive to parts of the body.

The gel substrate is not particularly limited as long as it gives water retaining properties and/or shape retainability to the adhesive layer. Examples thereof include organic gel substrates and inorganic gel substrates. One of these gel substrates may be used alone, or two or more of them may be used in combination.

Non-limiting examples of the organic gel substrates include thickening polysaccharides such as carrageenan, alginic acid, propylene glycol alginate, tara gum, locust bean gum, glucomannan, xanthan gum, welan gum, pectin, pullulan, guar gum, *psyllium* seed gum, welan gum, sodium alginate, mannan, gelatin, agar, casein, dextran, dextrin, soluble starch, carboxylated starch, methyl cellulose, ethyl cellulose, hydroxymethyl cellulose, hydroxyethyl cellulose, hydroxypropyl cellulose, ethyl hydroxyethyl cellulose, carboxymethyl cellulose, hydroxymethyl ethyl cellulose, methyl hydroxypropyl cellulose, hydroxypropyl cellulose phthalate, methyl cellulose, cellulose acetate, cellulose acetate and hydroxymethyl ethyl cellulose; polyacrylic acid polymers such as cross-linked polyacrylic acid, partially neutralized polyacrylic acid, polyacrylic acid-polymethacrylic acid copolymer and salts thereof (e.g., alkali metal salts such as sodium salt and potassium salt; salts of amine such as monoethanolamine, diethanolamine and triethanolamine; ammonium salts); rubber polymers such as polystyrene-polybutadiene-polystyrene copolymer, polystyrene-polyisoprene-polystyrene copolymer, polystyrene-polyethylene-polybutylene-polystyrene copolymer and polystyrene-polyethylene-polypropylene-polystyrene copolymer; and polyvinyl alcohol, carboxyvinyl polymer, urethane polymer and silicone polymer.

Of these gel substrates, organic gel substrates exhibit excellent adhesiveness and allow the adhesive layer to be closely attached to a part of the body which needs to be cooled. Thus, it is preferable that the gel substrate described in the present disclosure includes at least an organic gel substrate.

Non-limiting examples of inorganic gel substrates include double salts such as aluminum hydroxide, aluminum chloride, aluminum sulfate, aluminum nitrate, aluminum magnesium hydroxide, dihydroxyaluminum aminoacetate, kaolin and aluminum alum, and magnesium aluminometasilicate, smectite, montmorillonite, saponite, hectorite, bentonite, beidellite, nontronite, sauconite, stevensite, laponite and thickening silica.

Of them, at least one member selected from the group consisting of aluminum hydroxide, sodium polyacrylate, polyacrylic acid and polyvinyl alcohol is preferred. Use of such a gel substrate tends to improve sustained release of the cool feeling agent, local anesthetic and anti-inflammatory analgesic, and improve durability of the cool feeling effect and the analgesic effect. Furthermore, controlling vaporization of water tends to improve durability of the cool feeling effect.

Furthermore, another preferred embodiment of the gel substrate described in the present disclosure is a combination of an organic gel substrate and an inorganic gel substrate in order to improve shape retainability. In particular, a combination of aluminum hydroxide, sodium polyacrylate, polyacrylic acid and polyvinyl alcohol is preferred.

When an organic gel substrate and an inorganic gel substrate are used together as a gel substrate, their proportion is suitably determined depending on the type and the like of the organic gel substrate and the inorganic gel substrate to be used. For example, the proportion of the inorganic gel substrate is preferably 0.01 to 100 parts by weight, preferably 0.1 to 30 parts by weight, and preferably 1 to 10 parts by weight based on 100 parts by weight of the organic gel substrate.

The content of the gel substrate may be suitably determined based on water-retaining properties, shape retainability and the type of the gel substrate to be used. The content of the gel substrate is, for example, preferably 5 to 50% by weight, preferably 10 to 45% by weight, preferably 10 to 40% by weight, and particularly preferably 10 to 35% by weight based on the total amount of the adhesive layer.

Refreshing Agent

The adhesive layer of the present embodiment may also include a refreshing agent in addition to the cool feeling agent. When a refreshing agent is included, refreshing feeling can be given at the site where the patch is attached, and the cool feeling effect can be effectively felt.

The refreshing agent is not particularly limited, and examples thereof include camphor, borneol, thymol, spilanthol and methyl salicylate. One of these refreshing agents may be used alone, or two or more of them may be used in combination. Furthermore, a refreshing agent processed into particles with being adsorbed to organic or inorganic particles may also be used.

The content of the refreshing agent may be suitably determined depending on the level of refreshing feeling to be given and the like. For example, the content of the refreshing agent is preferably 0.001 to 10% by weight, preferably 0.01 to 5% by weight, and preferably 0.1 to 3% by weight.

pH Adjuster

The adhesive layer of the present embodiment may also include a pH adjuster. When a pH adjuster is included, the cool feeling effect and irritation can be adjusted.

The pH adjuster is not particularly limited, and examples thereof include organic acids such as tartaric acid, citric acid, lactic acid, gluconic acid, glycolic acid, malic acid, fumaric acid, methanesulfonic acid, maleic acid and acetic acid; and inorganic acids such as hydrochloric acid, phosphoric acid, sulfuric acid, nitric acid and hydrobromic acid. One of these pH adjusters may be used alone, or two or more of them may be used in combination.

The pH of the adhesive layer is preferably 4 to 7.4, preferably 4 to 7, preferably pH 4.5 to 7, and preferably 5.5 to 6.5. When the pH is in the above range, the cooling effect tends to be improved. Furthermore, irritation to the skin can be suppressed.

Other Components

The adhesive layer may include other components as necessary in addition to the components described above. Non-limiting examples of such components include blood circulation promoters such as acidic mucopolysaccharide, chamomile, *Aesculus hippocastanum*, ginkgo, *Hamamelis verginia* extract, grapefruit extract, rosemary extract, lemon extract, vitamin E and nicotinic acid derivatives; moisturizers such as glycerol, ceramide, collagen, hyaluronic acid and squalane; fatigue recovery agents such as basil extract and juniper extract; analgesics such as indomethacin, diclofenac, flurbiprofen, ketoprofen, piroxicam, felbinac, methyl salicylate and glycol salicylate; slimming agents such as tea extract, *ginseng* extract, caffeine, *Aesculus hippocastanum*, aminophylline, aescin, anthocyanidin, organic iodine compounds, *Hypericum erectum* extract, *Filipendula multijuga* extract, *Equisetum arvense, Rosmarinus officinalis, Hedera helix*, thiomucase and hyaluronidase; swelling reducing agents such as *Terminalia sericea, Ammi visnaga, Ammi majus, Aesculus hippocastanum*, anthocyanin, vitamin P, *Calendula officinalis*, concholytic acid and silanol; peeling agents such as proteases; hair-removing agents such as calcium thioglycolate; autonomic nerve-regulating agents such as γ-oryzanol; fragrances such as natural fragrances and single fragrances; antiseptics, disinfectants, antibacterial agents, colorants, moisturizers, irritation emollients, surfactants, solvents and sugar alcohols.

In one aspect, the maximum thickness H of the adhesive layer is 0.50, 0.55, 0.60, 0.65, 0.70, 0.75, 0.80, 0.85, 0.90, 1, 2, 3, 4, 5 mm or more. In another aspect, the maximum thickness H of the adhesive layer is 3.00, 2.90, 2.80, 2.70, 2.60, 2.50, 2.40, 2.30, 2.20, 2.10, 2.00, 1.95, 1.90, 1.85, 1.80, 1.75, 1.70, 1.65, 1.60, 1.55, 1.50, 2, 3, 4, 5, 6, 7, 8, 9, 10 mm or less. In some embodiments, the maximum thickness H of the adhesive layer is preferably 0.50 mm or more, preferably 0.75 mm or more, and preferably 1.00 mm or more. The upper limit of the maximum thickness H of the adhesive layer is not particularly limited, and is preferably 2.00 mm or less, preferably 1.75 mm or less, and preferably 1.50 mm or less. When the maximum thickness H of the adhesive layer is 0.50 mm or more, the amount of water contributing to cooling with heat of vaporization and heat capacity of the adhesive layer may be increased. Thus, the cool feeling effect and durability of the cool feeling effect may be improved. Furthermore, an increased thickness ensures sustained release of the cool feeling agent, the local anesthetic and the anti-inflammatory analgesic, improving durability of the cool feeling effect and the analgesic effect.

The maximum thickness of the adhesive layer refers to the maximum value of the thickness of the adhesive layer from the contact surface between the nonwoven fabric and the adhesive layer when the thickness of the adhesive layer varies in the surface direction of a patch. For the maximum thickness of the adhesive layer, for example, a patch is cut in the direction perpendicular to the surface direction, and the maximum thickness of the adhesive layer in the resulting cross-section may be measured with a caliper. Alternatively, the maximum thickness of the adhesive layer in a cross-section may be measured in an image of the cross-section photographed by, for example, a microscope.

In some embodiments, the area to which the adhesive layer is applied is smaller than the area of nonwoven fabric. In additional embodiments, the patch has, at the outer edge of nonwoven fabric, a non-applied portion to which no adhesive layer is applied. FIG. 1 shows a schematic view of a cross-section of a patch when the patch is attached to a target part S. As shown in FIG. 1, when there is a non-applied portion 12 to which no adhesive layer 2 is applied at the outer edge 11 of the nonwoven fabric 1, the nonwoven fabric 1 can cover the adhesive layer 2 in its entirety when a patch 10 is attached to the target part S. This may prevent the adhesive layer from being dried and shrunk from the side of the edge of the patch. This may also prevent uneven permeation of components including a local anesthetic and an anti-inflammatory analgesic due to, for example, shrinkage of the adhesive layer.

Figure 2:
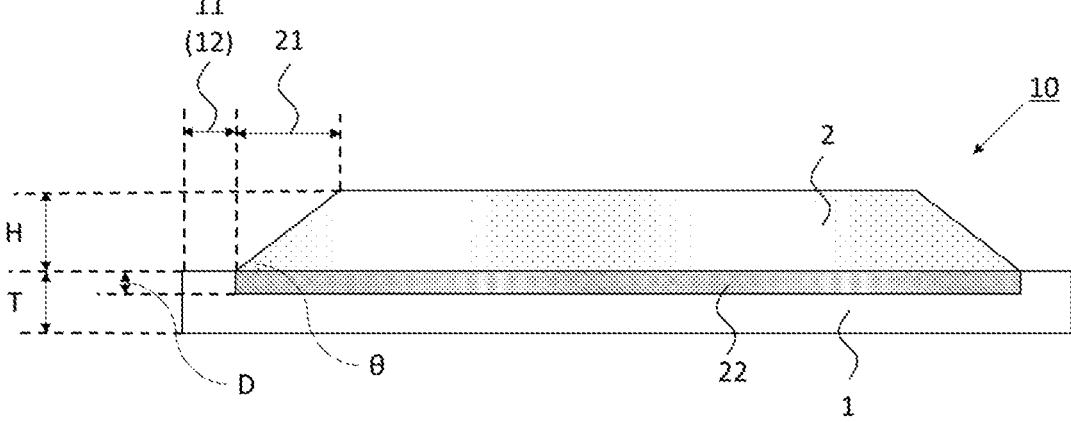
FIG. 2 shows a schematic view of a cross-section of an end portion of a patch according to an embodiment of the present invention.

FIG. 2 shows a schematic view of a cross-section of an end portion of a patch. As shown in FIG. 2, to be able to suppress drying and shrinkage of the adhesive layer from the side of the edge of a patch and to be able to prevent uneven permeation of components including a local anesthetic and an anti-inflammatory analgesic due to, for example, shrinkage of the adhesive layer, it is preferable that the adhesive layer 2 has an outer edge portion 21 whose thickness is gradually reduced toward the edge. In one aspect, the angle θ formed by a side surface of gel and the nonwoven fabric in the outer edge portion is 5, 6, 7, 8, 9, 10, 11, 12, 13, 14, 15, 16, 17, 18, 19, 20° or less. In another aspect, the angle θ formed by a side surface of gel and the nonwoven fabric in the outer edge portion is 90, 85, 80, 75, 70, 75, 60, 55, 50, 45° or less. In some embodiments, the angle θ formed by a side surface of gel and the nonwoven fabric in the outer edge portion is preferably 5° or more and less than 90°, preferably 10 to 60°, and preferably 10 to 45°. For angle θ, a patch is cut in the direction perpendicular to the surface direction and the angle θ in the resulting cross-section may be measured by using a protractor. Alternatively, the angle θ in a cross-section may be measured in an image of the cross-section photographed by, for example, a microscope.

The outer edge portion 21 may also be defined by its width. In one aspect, the width of the outer edge portion 21 may be 0.5, 0.6, 0.7, 0.8, 0.9, 1.0, 1.1, 1.2, 1.3, 1.4, 1.5 mm or more. In another aspect, the width of the outer edge portion 21 may be 1, 2, 3, 4, 5, 6, 7, 8, 9, 10, 11, 12, 13, 14, 15, 16, 17, 18, 19, 20, 21, 22, 23, 24, 25 mm or less. In some embodiments, the width of the outer edge portion 21 is preferably 0.5 to 25.0 mm, more preferably 1.0 to 23.0 mm, and further preferably 1.5 to 18.0 mm.

When the patch has such an outer edge portion, nonwoven fabric 1 can cover the whole part of the adhesive layer 2 as shown in FIG. 1, and thus the patch is unlikely to be detached. Furthermore, this can prevent the adhesive layer from being dried and shrunk from the side of the edge of the patch. This can also prevent uneven permeation of components including a local anesthetic and an anti-inflammatory analgesic due to, for example, shrinkage of the adhesive layer, and durability of the analgesic effect tend to be improved.

In one aspect, the adhesive layer has an adhesive force of 10, 20, 30, 40, 50, 60 gf/cm$^2$ or more. In another aspect, the adhesive layer has an adhesive force of 20, 30, 40, 50, 60, 70, 80, 90, 100 gf/cm$^2$ or less. In some embodiments, the adhesive layer has an adhesive force of preferably 10 to 100 gf/cm$^2$, preferably 20 to 70 gf/cm$^2$, and preferably 20 to 60 gf/cm$^2$. When the adhesive force of the adhesive layer is 10 gf/cm$^2$ or more, adhesion to the target part may be improved, and uneven permeation of components including a local anesthetic and an anti-inflammatory analgesic may be further suppressed. Furthermore, this tends to improve a cool feeling effect and an analgesic effect. When the adhesive force of the adhesive layer is 100 gf/cm$^2$ or less, it is more likely that remaining of an adhesive layer (remaining of gel) on the target part will be suppressed when the patch is removed.

Infiltration Layer

The patch of the present embodiment may also have an infiltration layer 22 in which part of the adhesive layer infiltrates into the nonwoven fabric. In the present embodiment, the "adhesive layer" refers to a portion which is not infiltrated into nonwoven fabric, and is distinguished from the infiltration layer. Thus, the thickness of the adhesive layer does not include the thickness of the infiltration layer.

In one aspect, the maximum thickness D of the infiltration layer is 0.001, 0.005, 0.010, 0.050, 0.100, 0.200, 0.300, 0.400 mm or more. In another aspect, the maximum thickness D of the infiltration layer is 0.005, 0.010, 0.050, 0.100, 0.200, 0.300, 0.400, 0.500 mm or less. In some embodiments, the maximum thickness D of the infiltration layer is preferably 0.001 to 0.500 mm, preferably 0.010 to 0.500 mm, and preferably 0.100 to 0.400 mm. When the maximum thickness D of the infiltration layer is 0.001 mm or more, the surface area of the gas-liquid interface of gel in the infiltration layer may be increased, and the cool feeling effect may be improved. Furthermore, when the maximum thickness D of the infiltration layer is 0.500 mm or less, the cool feeling effect may last long.

The maximum thickness of the infiltration layer refers to the maximum value of the depth of infiltration from the contact surface between the nonwoven fabric and the adhesive layer when the thickness of the infiltration layer varies in the surface direction of a patch. For the maximum thickness of the infiltration layer, for example, a patch is cut in the direction perpendicular to the surface direction, and the maximum thickness of the infiltration layer in the resulting cross-section may be measured with a caliper. Alternatively, the maximum thickness of the infiltration layer in a cross-section may be measured in an image of the cross-section photographed by, for example, a microscope.

Release Layer

The patch of the present embodiment may also have a peelable release layer on the side of the adhesive layer, which is attached to the skin. When the patch has a release layer, the adhesive layer can be kept hygienic until the patch is used, and handleability can be improved. The release layer is removed by peeling when the patch is used.

The material of the release layer is not particularly limited, and examples thereof include resin films such as polyethylene terephthalate, polyacrylonitrile, ethylene-vinyl alcohol copolymer and polypropylene; and paper which has been processed to be releasable by silicone processing and the like. When a resin film is used as the release layer, the film may also be processed to be releasable by silicone processing and the like.

Method of Production

The patch of the present embodiment may be produced by applying a composition containing components constituting the adhesive layer to non-woven fabric.

Purposes and Method of Use

The patch of the present embodiment is applied to a part of the body such as the skin, which requires a local anesthetic action, an anti-arrhythmic action, an action for preventing bronchoconstriction and an analgesic action against neuropathic pain and which needs to be cooled for a long time. More specifically, the patch of the present disclosure may be used as a coolant for the neck, a coolant for the eye, a coolant for the face, a coolant for the leg, a coolant for the shoulder, a coolant for the lower back, a coolant for tightening of the skin, a coolant used after exercise, and a coolant for inflammatory conditions such as bruises and sprain. In particular, the patch of the present disclosure is suitably used at an affected part which is immediately after being bruised and has heat, and needs to be cooled.

11

EXAMPLES

Hereinafter the present invention will be described in detail with reference to Examples and Comparative Examples. The present invention is not limited to the following Examples.

The patches of Examples 1 to 8 and Comparative Examples 1 to 4 were prepared according to the formulation shown in Tables 1 and 2. More specifically, the respective components of a gel substrate were gradually added to purified water and mixed. Then, a cool feeling agent, and a local anesthetic or an anti-inflammatory analgesic were added thereto to give a gel composition. The gel composition prepared as described above was applied to nonwoven fabric with a knife coater. A piece of polypropylene film, which serves as a release layer, was pressure-bonded thereto to prepare a patch.

The maximum thickness of the adhesive layer and the thickness of the infiltration layer of the patches of Examples were measured in an image of a cross-section of the patches photographed by a microscope. Furthermore, the angle formed by a side surface of gel and the nonwoven fabric in the outer edge portion was measured by using a protractor in the cross-section of the patches.

The adhesive force of the adhesive layer of the patches was measured by a compression tester (made by KATO TECH Co., Ltd., product name: KES-G5). The measurement conditions are shown below. The adhesive force ($gf/cm^2$) of the adhesive layer of the patches was calculated as an average value of the adhesive forces measured at five different points in the adhesive layer of the patches.

Rate: 0.10 cm/sec
Interval of capture: 0.1 sec
Upper limit of load: 50 $gf/cm^2$
Compression sensor: Probe having a pressurizing area of 2.0 $cm^2$ As a result, the angle formed by a side surface of gel and the nonwoven fabric in the outer edge portion was about 15° and the thickness of the infiltration layer was 0.3 mm.

TABLE 1

| | | Example | | | | | | | |
|---|---|---|---|---|---|---|---|---|---|
| | | 1 | 2 | 3 | 4 | 5 | 6 | 7 | 8 |
| Local anesthetic | Lidocaine | 2 | 4 | 4 | 4 | | | | |
| Anti-inflammatory analgesic | Ibuprofen | | | | | 5 | 5 | | |
| | Diclofenac | | | | | | | 1 | 1 |
| Cool feeling agent | Menthol | 0.5 | 1 | 1 | 3 | 1 | 1 | 1 | 1 |
| Gel substrate | Aluminum hydroxide | 0.4 | 0.4 | 0.4 | 0.4 | 0.4 | 0.4 | 0.4 | 0.4 |
| | Sodium polyacrylate | 5.6 | 5.6 | 5.6 | 5.6 | 5.6 | 5.6 | 5.6 | 5.6 |
| | Polyacrylic acid | 1.3 | 1.3 | 1.3 | 1.3 | 1.3 | 1.3 | 1.3 | 1.3 |
| | Polyvinyl alcohol | 6 | 6 | 6 | 6 | 6 | 6 | 6 | 6 |
| | L-tartaric acid | 0.1 | 0.1 | 0.1 | 0.1 | 0.1 | 0.1 | 0.1 | 0.1 |
| | Methylparabene | 0.05 | 0.05 | 0.05 | 0.05 | 0.05 | 0.05 | 0.05 | 0.05 |
| | Dipropylene glycol | 7.8 | 7.8 | 7.8 | 7.8 | 7.8 | 7.8 | 7.8 | 7.8 |
| | Grycerol | 4 | 4 | 4 | 4 | 4 | 4 | 4 | 4 |
| | Propylparabene | 0.02 | 0.02 | 0.02 | 0.02 | 0.02 | 0.02 | 0.02 | 0.02 |
| | Polysolbate 80 | 1 | 1 | 1 | 1 | 1 | 1 | 1 | 1 |
| | Polyethylene glycol 40 | 3 | 3 | 3 | 3 | 3 | 3 | 3 | 3 |
| Water | Purified water | 68.23 | 65.73 | 65.73 | 63.73 | 64.73 | 64.73 | 68.73 | 68.73 |
| Total (% by weight) | | 100 | 100 | 100 | 100 | 100 | 100 | 100 | 100 |
| Amount coated (g) | | 12 | 6 | 12 | 12 | 6 | 12 | 6 | 12 |
| Thickness of adhesive layer (mm) | | 1.00 | 0.50 | 1.00 | 1.00 | 0.50 | 1.00 | 0.50 | 1.00 |
| Thickness of infiltration layer (mm) | | 0.300 | 0.250 | 0.200 | 0.100 | 0.200 | 0.200 | 0.300 | 0.300 |
| Adhesive force ($gf/cm^2$) | | 28 | 28.5 | 29 | 27.4 | 28 | 28.3 | 28.7 | 27.8 |
| Total amount of local anesthetic and anti-inflammatory analgesic (g) | | 0.24 | 0.24 | 0.48 | 0.48 | 0.3 | 0.6 | 0.06 | 0.12 |
| Total amount of cool feeling agent (g) | | 0.06 | 0.06 | 0.12 | 0.36 | 0.06 | 0.12 | 0.06 | 0.12 |
| Cool feeling agent/(local anesthetic + anti-inflammatory analgesic) | | 25 | 25 | 25 | 75 | 20 | 20 | 100 | 100 |
| Test of cool feeling | Cool feeling (immediately after attachment) | A | A | A | A | A | A | A | A |
| | Cool feeling (3 hours after attachment) | B | C | B | A | B | B | B | B |
| Test of analgesic effect | Analgesic effect (2 hours after attachment) | A | B | A | A | C | B | B | A |

TABLE 2

| | | Comparative Example | | | |
|---|---|---|---|---|---|
| | | 1 | 2 | 3 | 4 |
| Local anesthetic | Lidocaine | 4 | 4 | | |
| Anti-inflammatory analgesic | Ibuprofen | | | 5 | |
| | Diclofenac | | | | 1 |
| Cool feeling agent | Menthol | 1 | | 1 | 1 |
| Gel substrate | Dihydroxyaluminum aminoacetate | 0.4 | | | |
| | Aluminum hydroxide | 0.3 | | 0.4 | 0.4 |
| | Sodium carboxymethyl cellulose | 13 | | | |

TABLE 2-continued

| | | Comparative Example | | | |
| --- | --- | --- | --- | --- | --- |
| | | 1 | 2 | 3 | 4 |
| | Aluminum silicate | | 0.5 | | |
| | Dihydroxyaluminum aminoacetate | | 0.3 | | |
| | Disodium edetate | | 0.01 | | |
| | Gelatin | | 24 | | |
| | Oleic acid | | 7.5 | | |
| | Sodium polyacrylate | | | 5.6 | 5.6 |
| | Polyacrylic acid | | | 1.3 | 1.3 |
| | Polyvinyl alcohol | | | 6 | 6 |
| | L-tartaric acid | 0.2 | 0.25 | 0.1 | 0.1 |
| | Methylparabene | 0.1 | | 0.05 | 0.05 |
| | Dipropylene glycol | | | 7.8 | 7.8 |
| | Grycerol | 7 | | 4 | 4 |
| | Propylparabene | | 0.07 | 0.02 | 0.02 |
| | Polysolbate 80 | 4 | | 1 | 1 |
| | Polyethylene glycol 40 | | | 3 | 3 |
| | Silicon dioxide | 0.01 | | | |
| | Urea | 1 | | | |
| | Titanium oxide | 0.06 | 0.1 | | |
| | Castor oil | 5 | | | |
| | Propylene glycol | 4 | 8 | | |
| | Polyoxyl 40 hydrogenated castor oil | 6.5 | | | |
| Water | Purified water | 53.43 | 55.27 | 64.73 | 68.73 |
| Total (% by weight) | | 100 | 100 | 100 | 100 |
| Amount coated (g) | | 6 | 14 | 6 | 6 |
| Thickness of adhesive layer (mm) | | 0.2 | 0.8 | 0.2 | 0.2 |
| Thickness of infiltration layer (mm) | | 0.005 | 0.01 | 0.2 | 0.3 |
| Adhesive force (gf/cm$^2$) | | 26.9 | 40.1 | 28.3 | 28.6 |
| Total amount of local anesthetic and anti-inflammatory analgesic (g) | | 0.24 | 0.56 | 0.3 | 0.06 |
| Total amount of cool feeling agent (g) | | 0.06 | 0 | 0.06 | 0.06 |
| Cool feeling agent/(local anesthetic + anti-inflammatory analgesic) | | 25 | 0 | 20 | 100 |
| Test of cool feeling | Cool feeling (immediately after attachment) | A | C | A | A |
| | Cool feeling (3 hours after attachment) | D | D | C | C |
| Test of analgesic effect | Analgesic effect (2 hours after attachment) | C | C | D | C |

Test of Cool Feeling

Each of the patches of Examples and Comparative Examples prepared as described above was attached to the lower back of 10 testers. Cool feeling was evaluated immediately after attachment and 3 hours after attachment. More specifically, cool feeling was evaluated based on 11 divided numerical rating scales of 0 to 10, which indicate the level of current cool feeling, with 0 being no cool feeling and 10 the maximum cool feeling assumed. The results of evaluation of the testers were averaged and rounded off to 2 decimal places. Cool feeling was evaluated based on the following evaluation criteria.

Evaluation Criteria

A: An average mark of 8 or more.
B: An average mark of 6 or more and less than 8
C: An average mark of 5 or more and less than 6
D: An average mark of less than 5.

Method of Evaluation: Test of Analgesic Effect

Each of the patches of Examples and Comparative Examples prepared as described above was attached to the lower back of 10 testers who have lower back pain. An analgesic effect was evaluated 2 hours after attachment. More specifically, the analgesic effect was evaluated based on 11 divided numerical rating scales of 0 to 10, which indicate the level of current pain, with 0 being no pain and 10 the maximum pain assumed. The results of evaluation of the testers were averaged and rounded off to 2 decimal places. The analgesic effect was evaluated based on the following evaluation criteria.

Evaluation Criteria

A: An average mark of less than 5.
B: An average mark of 5 or more and less than 6.
C: An average mark of 6 or more and less than 8
D: An average mark of 8 or more.

The invention claimed is:
1. A patch comprising:
a nonwoven fabric;
an adhesive layer on the nonwoven fabric; and
an infiltration layer between the adhesive layer and the nonwoven fabric;
wherein the adhesive layer comprises (i) a cool feeling agent, (ii) a local anesthetic and/or an anti-inflammatory analgesic, and (iii) water,
a content of the cool feeling agent comprises 6.25 to 500 parts by weight based on a total of 100 parts by weight of the local anesthetic and the anti-inflammatory analgesic,
the adhesive layer has a maximum thickness of 0.50 mm to 10 mm, the infiltration layer has a maximum thickness of 0.001 to 0.500 mm, an area of the nonwoven fabric to which the adhesive layer is applied is smaller than a total area of the nonwoven fabric, and the adhesive layer has an outer edge portion whose thickness is gradually reduced toward an edge such that an angle formed by a side surface of the adhesive layer and the nonwoven fabric in the outer edge portion is 5° or more and less than 90°.

2. The patch according to claim 1, wherein the local anesthetic comprises lidocaine.

3. The patch according to claim 1, wherein the cool feeling agent comprises menthol.

4. The patch according to claim 1, wherein the adhesive layer has an adhesive force of 10 to 100 gf/cm$^2$.

5. The patch according to claim 1, wherein the adhesive layer has a maximum thickness of 0.75 mm to 10 mm.

6. The patch according to claim 1, wherein a content of the cool feeling agent comprises 0.01 to 10% by weight based on a total amount of the adhesive layer.

7. The patch according to claim 1, wherein a total content of the local anesthetic and the anti-inflammatory analgesic is 1 to 7.5% by weight based on a total amount of the adhesive layer.

8. The patch according to claim 1, wherein a content of the water is 50 to 90% by weight based on a total amount of the adhesive layer.

9. The patch according to claim 1, wherein the adhesive layer comprises at least one member selected from the group consisting of aluminum hydroxide, sodium polyacrylate, polyacrylic acid and polyvinyl alcohol.

10. The patch according to claim 1, wherein the adhesive layer has a maximum thickness of 1.00 mm to 10 mm.

11. The patch according to claim 1, wherein the content of the cool feeling agent is 10 to 150 parts by weight based on a total of 100 parts by weight of the local anesthetic and the anti-inflammatory analgesic.

12. The patch according to claim 1, wherein the content of the cool feeling agent is 20 to 125 parts by weight based on a total of 100 parts by weight of the local anesthetic and the anti-inflammatory analgesic.

13. The patch according to claim 1, wherein a total content of the local anesthetic is 1 to 7.5% by weight based on a total amount of the adhesive layer.

14. The patch according to claim 1, wherein the infiltration layer has a maximum thickness of 0.200 to 0.500 mm.

15. The patch according to claim 1, wherein the adhesive layer has a maximum thickness of 0.5 mm to 1 mm.

16. The patch according to claim 1, wherein the angle formed by a side surface of the adhesive layer and the nonwoven fabric in the outer edge portion is 5° or more and less than 20°.

17. The patch according to claim 1, wherein the adhesive layer has an adhesive force of 20 to 30 gf/cm$^2$.

18. The patch according to claim 1, wherein the nonwoven fabric has a thickness of 0.50 to 5.00 mm.

19. The patch according to claim 1, wherein a width of the outer edge portion is 0.5 to 25 mm.

* * * * *